United States Patent [19]
Seriguchi et al.

[11] Patent Number: 5,728,056
[45] Date of Patent: Mar. 17, 1998

[54] LUMBAGO CORRECTING BELT

[75] Inventors: Fukumori Seriguchi, Nobeoka; Toshimichi Shirouzu, Akashi; Terusato Yamada; Takefumi Nakashita, both of Kobe, all of Japan

[73] Assignee: Sumitomo Rubber Industries, Ltd., Hyogo-ken, Japan

[21] Appl. No.: 701,133

[22] Filed: Aug. 21, 1996

[30] Foreign Application Priority Data

Aug. 22, 1995 [JP] Japan ................................ 7-213741
Nov. 7, 1995 [JP] Japan ................................ 7-288766

[51] Int. Cl.$^6$ ................................................ A61F 5/00
[52] U.S. Cl. ................................................... 602/19
[58] Field of Search ......................................... 602/19

[56] References Cited

U.S. PATENT DOCUMENTS

| | | | |
|---|---|---|---|
| 3,570,480 | 3/1971 | Stubbs | 602/19 |
| 4,459,979 | 7/1984 | Lewis, Jr. | 602/19 |
| 4,475,543 | 10/1984 | Brooks et al. | 602/19 |
| 5,548,843 | 8/1996 | Chase et al. | 602/19 X |

*Primary Examiner*—Linda C. Dvorak
*Attorney, Agent, or Firm*—Nikaido Marmelstein Murray & Oram LLP

[57] ABSTRACT

A lumbago correcting belt is disclosed, comprising a belt body adapted to be attached to a lumbar region of a human body to enclose and surround the iliac bones and a pair of tightening members made of a flexible material the tightening members being disposed and spaced from each other on an outer circumferential face of the belt body. Each of the tightening members has two legs branched therefrom which compress the iliac bones by a tightening force selectively given to only one of the two legs. In one embodiment, a first set of engaging means is provided, one member of which is provided at one end portion of the belt body on an outer circumferential face thereof and another member of which is provided at the other end portion of the belt body on an inner circumferential face thereof, and a second set of engaging means is provided on the tightening members at one face of front end portions thereof. In a second embodiment, a first set of engaging means is provided, a first member of which is provided at one end portion of the belt body on he outer circumfential face thereof, a second member of which is provided at the other end portion of the belt body on the outer circumferential face thereof, a third member of which is provided at the other end portion of the belt body on an inner circumferential face thereof and a fourth member of which is provided at a middle portion of the belt body on the outer circumferential face thereof and a second set of engaging means is provided on he tightening members at both faces of front end portions thereof.

20 Claims, 8 Drawing Sheets

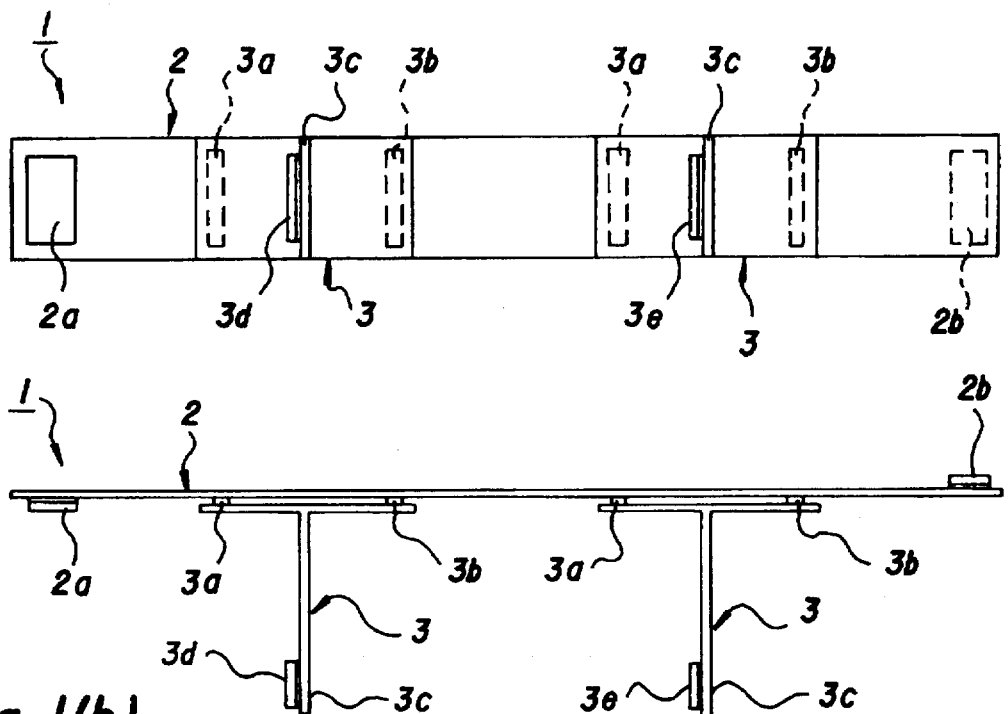
Fig.1(a)
Fig.1(b)
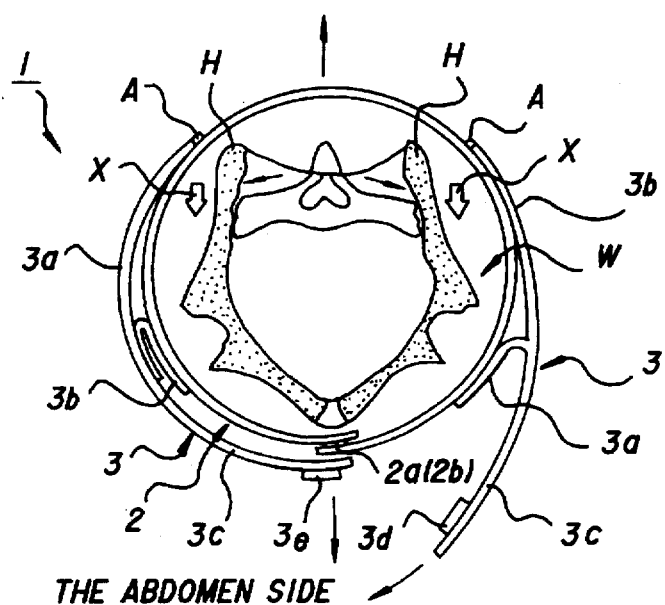
Fig.2
THE BACK SIDE
THE ABDOMEN SIDE

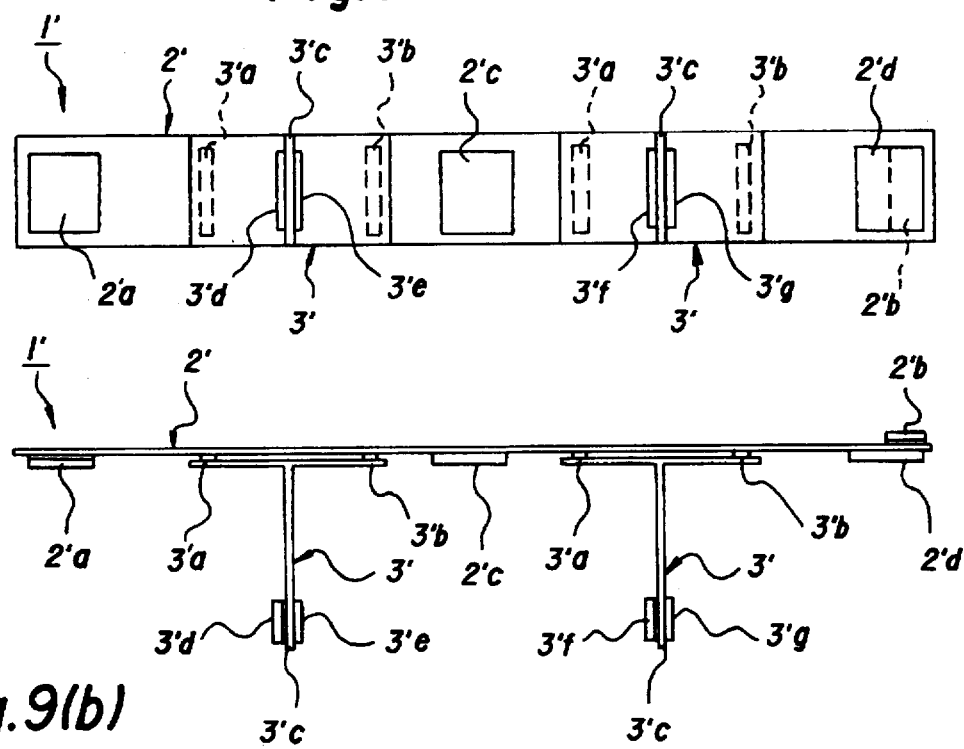
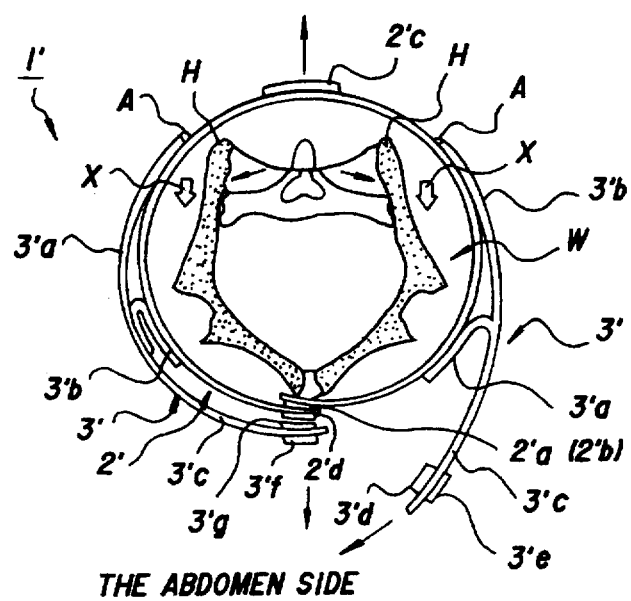

LUMBAGO CORRECTING BELT

BACKGROUND OF THE INVENTION

The present invention relates to a lumbago correcting belt which is used for preventing and treating lumbago. There is a means for attaching a belt to a lumbar region subjected to lumbago, as one of means for treating lumbago. For example, as this kind of belt, a lumbago region belt (Japanese laid-open patent No. Hei-6-78943) provided with a sub material having a shock absorbing property and a supporting property almost at the middle part of the belt body make of a flexible material, and health promoting belt (Japanese laid-open utility model No. Hi-2-28222) at which a plate-like treating member made of a far-infrared radiation ceramic is movably provided at a belt body to be wound on a lumbar region are proposed.

Primary objects to use this kind of belt are correcting a lumbar vertebra slip, lightening a weight load given to the lumbar region, stabilizing the pelvis by tightening the pelvis, and protection around the loins, and a conventional lumbago belt is such that each of the abovementioned four functions is adjusted on the basis of the state of the lumbago.

In addition to the above two examples, various kinds of belts have been proposed. However, each of such belts only indirectly lightens lumbago by merely stabilizing the state around the loins and attempting to reduce the weight load. That is, conventional belts lighten pain by stabilizing the state around the loins and only expect treatment by a self-curing action. Such belts are not able to fundamentally treat lumbago.

It is therefore an object of the invention to provide a lumbago correcting belt which is able to fundamentally treat lumbago.

SUMMARY OF THE INVENTION

Recently, it has been found that one of major causes of lumbago is the interval between the iliac bones being too wide or too narrow due to slipping or straining of a pair of left and right iliac bones.

The inventors assumed that lumbago is able to be fundamentally treated if a slip or the like of the iliac bones, which will be a cause of lumbago, is corrected by a belt, and carried out various kinds of experiments in order to verify this. As a result, they found and confirmed that, by compressing the iliac bones from the left and right back side of the lumbar region when the interval between the iliac bones is made narrower or compressing the iliac bones from the left and right front side when the interval therebetween is made wider, the interval between the iliac bones is able to be adjusted to a good health value (appointed value) and finally lumbago is able to be remarkably efficiently lightened.

Based on the results of the abovementioned experiments, a lumbago correcting belt according to the invention has such a construction that lumbago can be fundamentally treated by adjusting the interval between the iliac bones. That is, the lumbago correcting belt of the invention is provided with a belt body to be detachably attached to the lumbar region of a human body so that the same encloses an surrounds the iliac bones, and a pair of band-like tightening members, made of a flexible material, which are disposed and spaced from each other at appointed parts on the outer circumferential face of the belt body and compress the iliac bones from an appointed direction of the lumbar region.

The belt body may be constructed so that engaging means are provided at one end portion of the outer circmferential face and the other end portion of the inner circumferential face of the belt body, and engaging means are provided at one face of the front end portions of the pair of tightening members. In this case, when wearing the belt on the lumbar region, the belt body is wound on the lumbar region and tightened by an adequate tightening force, and thereafter the engaging means provided at the end portion of the outer circumferential face thereof and at the end portion of the inner circumferential face thereof are engaged with each other. After the belt body is thus attached to the lumbar region, the pair of tightening members are elongated so as to obtain an adequate tightening force, and the engaging means thereof are engaged with each other at the abdomen side of the lumbar region, whereby the iliac bones are compressed from the left and right back side of the lumbar region. In other way, when causing the engaging means of the pair of tightening members to be engaged with each other at the back side of the lumbar region, the iliac bones are compressed from the left and right front side of the lumbar region.

With the lumbago correcting belt of the invention, it is possible to stabilize the state around the loins as by a conventional belt since the lumbar region is tightened by the belt body. In addition, it is possible to adjust the interval between the iliac bones by causing the pair of tightening members to be engaged with each other at the abdomen side or back side of the lumbar region while elongating the same. For example, if a person feels a pain at the lumbar region when he bends himself back, the interval between the iliac bones is widened by causing the tightening members to be engaged with each other at the abdomen side, and if he feels a pain when he leans forward, the interval between the iliac bones is closed by causing the tightening members to be engaged with each other at the back side. Thus, the lumbago correcting belt of the invention can be used with a properly use mode according to the symptoms of lumbago. Resultantly, it is possible to correct slips or strains of the iliac bones, which is one of causes of lumbago, and to adjust the interval between the iliac bones to a good health value (normal value), whereby to fundamentally treat lumbago remarkably efficiently. Furthermore, if a lumbago correcting belt of the invention is worn when a slip or the like is going to occur, it is possible to prevent lumbago.

As described above, a lumbago correcting belt of the invention is able to bring us sufficient effects when feeling a pain when bending back or leaning forward. Further the lumbago correcting belt of the invention may be provided with engaging means at both end portions and the middle portion of the outer circumferential face and one end portion of the inner circumferential face of the belt body, and engaging means at both faces of the front end portions of the tightening members, so as to be able to cope with a case where a person feels a pain when twisting the lumbar region leftward or rightward. In this case, when attaching said lumbago correcting belt, after the belt body is wound onto the lumbar region and tightened with an adequate force, the engaging means provided at the end portion of the outer circumferential face thereof and the engaging means provided at the end portion of the inner circumferential face thereof are engaged with each other. And after the belt body is thus attached to the lumbar region, one of he engaging means of the pair of tightening members is engaged with the engaging means provided at the middle portion on the outer circumferential face of the belt body, and the other engaging means of the pair of tightening members is engaged with one of the engaging means provided at both end portions of the outer circumferential face of the belt body, whereby the iliac bones are compressed in the leftward twisting direction relative to the lumbar region or in the rightward twisting direction relative to the lumbar region.

For example, when feeling a pain when twisting leftward, the pair of tightening members are engaged with the belt body at the back side and abdomen side so as to cause the tightening members to be turned rightward relative to the lumbar region, and when feeling a pain when twisting rightward, a pair of tightening members are engaged with the belt body at the abdomen side and back side so as to cause the tightening members to be turned leftward relative to the lumbar region, whereby the interval between the iliac bones are adjusted to a good health value. Thus, the lumbago correcting belt of the invention can be used with a properly use mode according to the symptoms of lumbago. As a matter of course, it is possible to compress the iliac bones from the left and right front side of the lumbar region by causing a pair of tightening members to be engaged with each other at the abdomen side of the lumbar region, or to compress the iliac bones from the left and right front side of the lumbar region by causing them to be engaged with each other at the back side.

Still furthermore, a pair of tightening members may be movably disposed at an appointed position on the outer circumferential face of the belt body.

BRIEF DESCRIPTION OF THE DRAWINGS

FIG. 1(a) is a front elevational view showing a first preferred embodiment, and FIG. 1(b) is a plan view thereof.

FIG. 2 is a view showing a use mode for a patient whose interval between the iliac bones is made narrower.

FIG. 9(a) is a front elevational view showing a second preferred embodiment of the invention, and FIG. 9(b) is plan view thereof.

FIG. 10 is a view showing a use mode for a patient whose interval between the iliac bones is made narrower.

DESCRIPTION OF PREFERRED EMBODIMENTS

Figure 3:
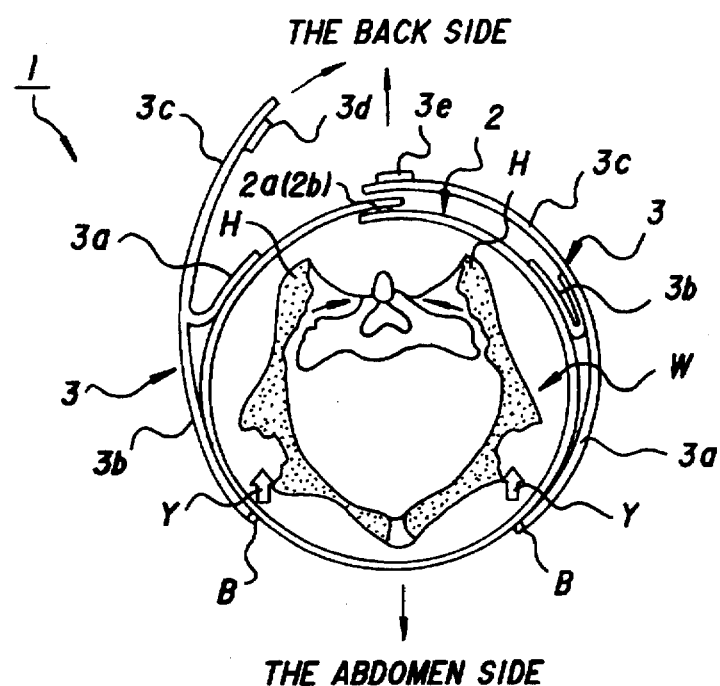
FIG. 3 is a view showing a use mode for a patient whose interval between the iliac bones is made wider.

Preferred embodiments of the invention are described below.

Firstly, with reference to FIG. 1 to FIG. 4, a description will be given of the first preferred embodiment of the invention. A lumbago correcting belt 1 of the first preferred embodiment comprises a band-like belt body 2 having an adequate flexibility and detachably attached to the lumber region W of a human body so as to enclose and surrounds the iliac bones H, H, and a pair of tightening members 3 disposed and spaced from each other at an appointed portions of the outer circumferential face of the belt body 2.

The belt body 2 may be of a flexible or non-flexible material, however, it is preferably of a nylon base material having a good ventilation property. Furthermore, only the middle portion thereof may be of a flexible material and the other portion thereof may be of a non-flexible material. A face fastener 2a is stitched at or adhered to one end portion on the outer circumferential face of the belt body 2 as an engaging means, and a face fastener 2b is stitched at or adhered to the other end portion on inner circumferential face thereof as an engaging means.

A pair of tightening members 3 are disposed on the outer circumferential face of the belt body 2 with an interval equivalent to a half turn of the lumber region. The tightening member 3 which has a band-like member 3c protruding from the boundary portion of flat portions 3a, 3b is, for example, as shown in FIG. 1(b), formed to be T-shaped on the plan view thereof. A flexible material having a moderate rigidity and a good durability is preferable for the tightening member 3. As one example of such a material, a natural rubber may be listed. The flat portions 3a, 3b (both-end portion) of a tightening member 3 are stitched at or adhered to the outer circumferential face of the belt body 2, and face fasteners 3d, 3e, as engaging means which are engageable with each other, are respectively stitched at or adhered to one side of the front end portion of the band-like member 3c of the tightening member 3.

A lumbago correcting belt 1 of this embodiment may be used for treating and preventing lumbago as shown below. For example, in a case of a patient whose interval between the iliac bones H, H is made narrow, as shown in FIG. 2, after the belt body 2 is wound on and around the lumbar region W and is tightened with an adequate force, the face fasteners 2a, 2b thereof are engaged with each other at the abdomen side. And after the belt body 2 is thus attached to the lumbar region W, the band-like members 3c, 3c of the pair of tightening members 3 are elongated to be given adequate tightening forces (restoring forces) thereto, and the face fasteners 3d, 3e thereof are engaged with each other at the abdomen side. The iliac bones H, H are compressed by tightening forces of the elongated tightening members 3, 3 so as to be pushed out in the directions of the arrow (X) from the back side, whereby the interval between the iliac bones may be widened to a good health value (normal value).

Figure 4:
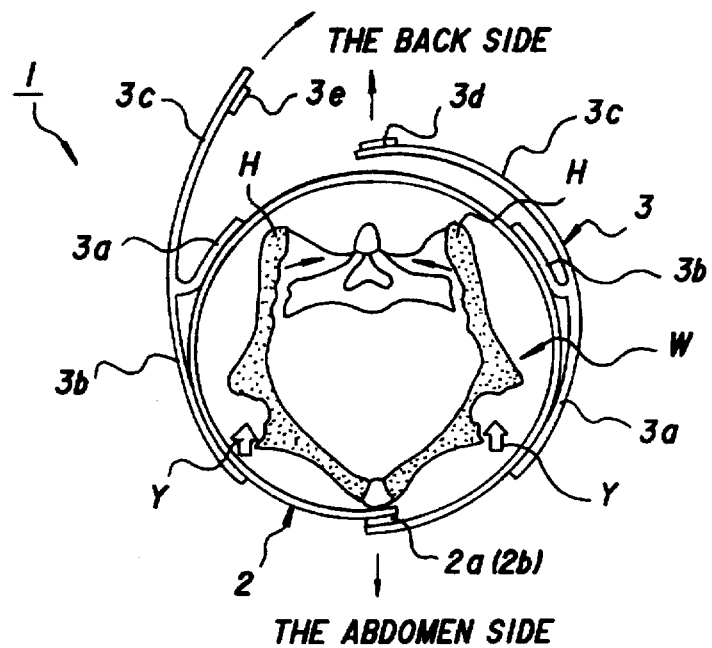
FIG. 4 is a view showing a use mode for a patient whose interval between the iliac bones is made wider.

On the other hand, in a case of a patient whose interval between the iliac bones H, H is widened, as shown in FIG. 3, the band-like members 3c, 3c of the pair of tightening members 3 are elongated to be given adequate tightening forces (restoring forces) thereto, and the face fasteners 3d, 3e thereof are elongated with each other at the back side. By tightening forces of the elongated tightening members 3, 3, the iliac bones H, H are compressed so as to be pushed out in the directions of the arrow (Y) from the abdomen side to cause the interval therebetween to be made narrow to a good health value. In addition, in FIG. 3, although the belt body 2 is engaged at the back side, the same may be engaged at the abdomen side as shown in FIG. 4.

According to a lumbago correcting belt 1 of the above-mentioned preferred embodiment, the lumbar region is stabilized by the belt body 2 as by a conventional belt, and it is possible to give force vectors starting from the diagonally rearward parts (parts (A) in FIG. 2) or diagonally frontward parts (parts (B) in FIG. 3) to the lumbar region W, by a tightening actions of the tightening members 3, 3. As a result, the iliac bones H, H are pushed out forward or backward, whereby the interval between the iliac bones H, H is adjusted to a good health value. Therefore, it is possible to fundamentally eliminate a cause of lumbago and to remarkably efficiently treat and prevent the same.

Furthermore, the tightening members 3, 3 may be disposed to be movable relative to the outer circumferential face of the belt body 2 so as to obtain an appointed tightening forces when the engaging members 3d, 3e of tighting members 3 are engaged with each other. As a means therefor, for example, the flat portions 3a, 3b of tightening members 3, 3 are detachable attached to the outer circumferential face of the belt body 2 with face fasteners or the like. By adequately slipping the positions of the tightening members 3, 3 relative to the belt body 2, it is possible to correct the tightening forces of the tightening members 3, 3 from becoming excessively intensive or weak.

FIG. 5 to FIG. 8 show modified examples of a tightening member in the first preferred embodiment described above. The other configuration thereof remains unchanged.

Figure 5:
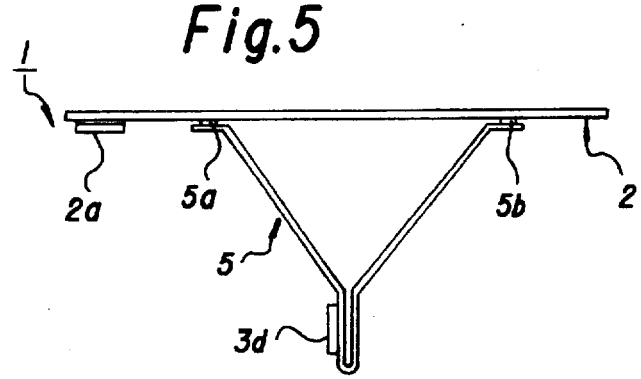
FIG. 5 is a partially enlarged plan view showing a modified example of a tightening member.

A tightening member 5 shown in FIG. 5 is formed to be bifurcated, using a rubber plate or rubber tube, and the flat portions 5a, 5b are fixed on the outer circumferential face of the belt body 2 with their interval slightly widened. Since this modified example is such that the flat portions 5a, 5b are fixed on the belt body 2 with their interval widened, it is possible to uniformly tighten the iliac bones H, H in a wide range.

Figure 6:
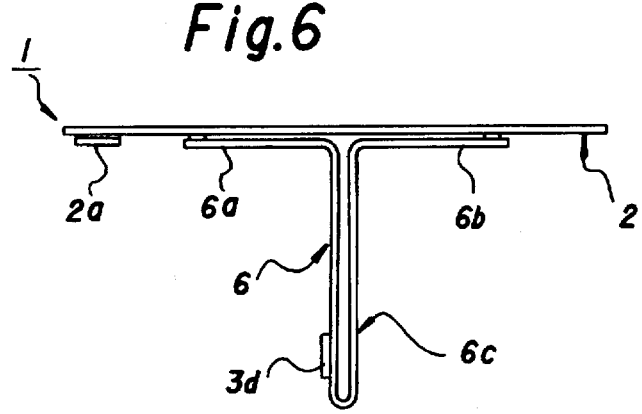
FIG. 6 is a partially enlarged plan view showing a modified example of a tightening member.

A tightening member 6 shown in FIG. 6 is such that the band-like member 6c at the boundary portion between the flat portions 6a, 6b is formed to be double. Therefore, the tightening force of the tightening member 6 is stronger than that of tightening members 3, 5 already described, and the durability thereof is better.

Figure 7A:
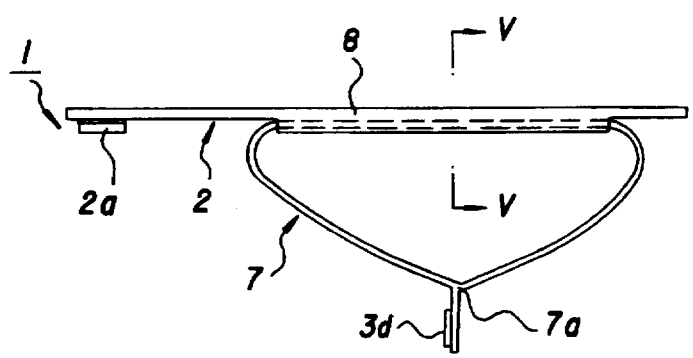
FIG. 7(a) is a partially enlarged plan view showing a modified example of tightening member.
Figure 7C:
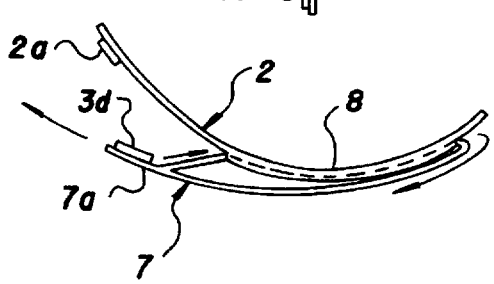
FIG. 7(c) is a partially enlarged plan view showing a state where a lumbago correcting belt is attached to the lumbar region.
Figure 7B:
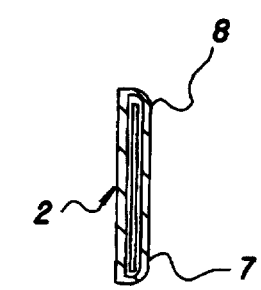
FIG. 7(b) is a cross-sectional view taken along the line V—V in FIG. 7(a)

A tightening member 7 shown in FIG. 7 is integrated at a joint 7a, is formed to be roughly annular and further is movably inserted into a sheathed part 8 disposed along the lengthwise direction of the belt body 2. Since, with this modified example, the tightening member 7 is able to slide in a direction that the joint 7a is elongated, it is possible to remarkably efficiently tighten the iliac bones H, H without producing any slackening at the tightening member 7.

Figure 8:
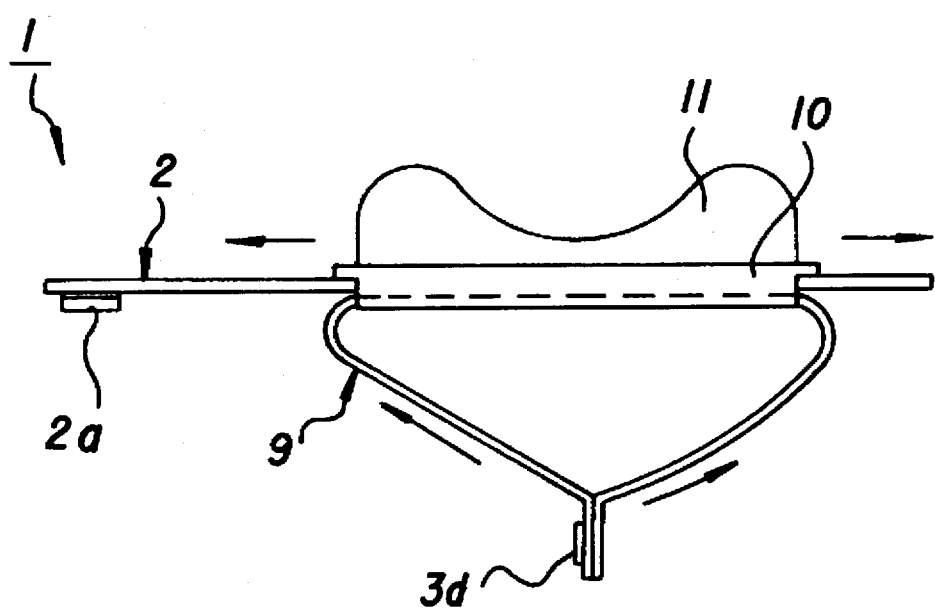
FIG. 8 is a partially enlarged plan view showing a modified example of a tightening member.

A tightening member 9 shown in FIG. 8 is inserted into a sheathed part 10 movably attached to an appointed position of the belt body 2, wherein the tightening member 9 is movably mounted in the sheathed part 10. Furthermore, a sponge 11 for loins fitting, the middle portion of which is slightly dented, is fixed inside he sheathed part 10. Therefore, the sheathed part 10 is adjusted to an optimal position according to the body figure of a patient, and the sponge 11 is put on the curved line of the lumbar region W, whereby it is possible to more securely adjust the interval between the iliac bones H, H.

Next, referring to FIG. 9 through FIG. 15, a description will be given below of a second preferred embodiment of the invention. Features of a lumbago correcting belt 1' of the second preferred embodiment in comparison with a lumbago correcting belt 1 of the first embodiment described above are that, as engaging means, face fasteners 2a', 2b', 2c' and 2d' are provided at both end portions and middle portion of the outer circumferential face of the belt body 2' and at one end portion of the inner circumferential face thereof, respectively and that as engaging means, face fasteners 3d', 3e', 3f and 3g' are provided at both the faces the front end portions of a pair of tightening members 3' respectively.

As regards the treatment and prevention of lumbago with this lumbago correcting belt 1', it is possible to selectively uses several use modes shown in FIG. 10 to FIG. 13 according to the symptom of a patient. For example, in a case where the interval between the iliac bones H, H is made narrow at the lumbar region (that is, when a patient feels a pain when bending himself back), as shown in FIG. 10, after the belt body 2' is wound round the lumbar region W and is tightened with adequate tightening forces, the face fasteners 2a', 2b' thereof are engaged with each other at the abdomen side. And after the belt body 2' is thus attached to the lumbar region W, the band-like members 3c', 3c' of the pair of tightening members 3' are elongated so as to obtain an adequate tightening forces (restoring forces), and face fasteners 3d', 3f thereof are mutually overlapped at the abdomen side and engaged with each other. Furthermore, at this time, the face fastener 3g' of the band-like member 3c' is engaged with the face fastener 2d' of the belt body 2'. By tightening forces of the tightening members 3', 3', the iliac bones H, H are compressed so as to be pushed out in the directions of the arrow (X) from the back side, whereby the interval between the iliac bones H, H is widened to a good health value.

Figure 11:
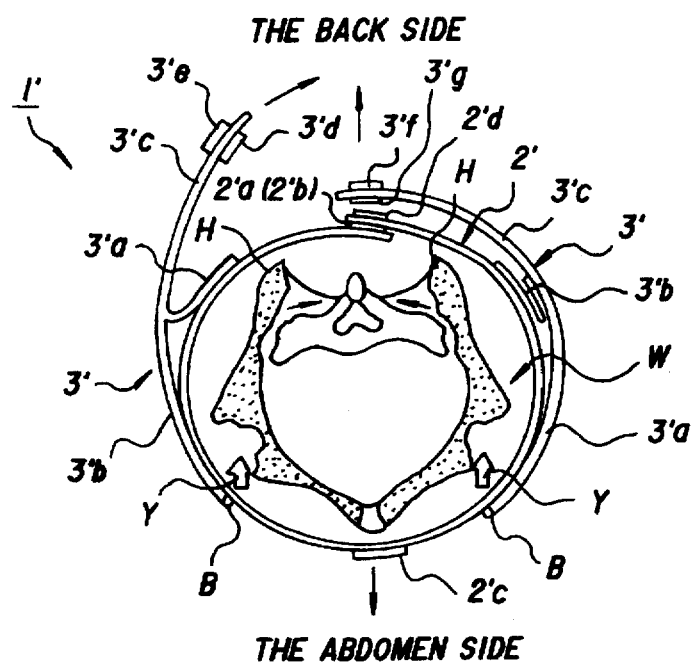
FIG. 11 is a view showing a use mode for a patient whose interval between the iliac bones is made wider.
Figure 12:
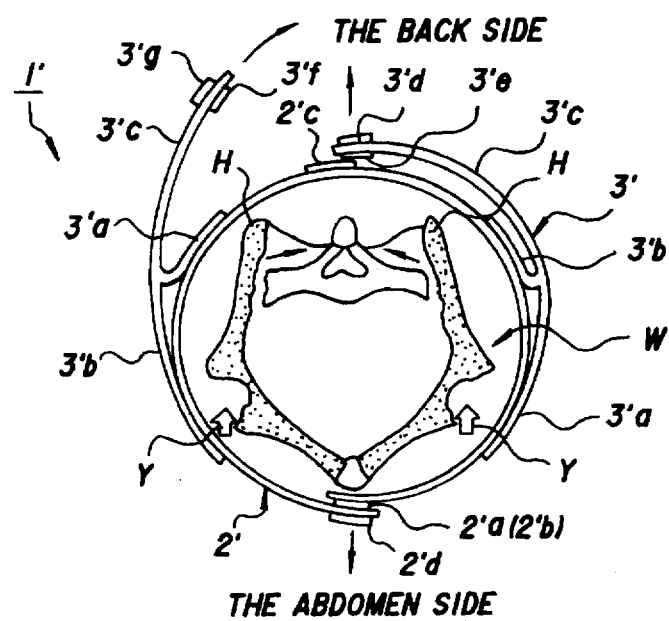
FIG. 12 is a view showing a use mode for a patient whose interval between the iliac bones is made wider.

In a case of a patient whose interval between the iliac bones H, H is widened, as shown in FIG. 11, after the belt body 2' is wound around the lumbar region W and is tightened with an adequate tightening force, the face fasteners 2a', 2b' thereof are engaged with each other at the back side. And after the belt body 2' is thus attached to the lumbar region W, the band-like members 3c', 3c' of the pair of tightening members 3' are elongated so as to obtain adequate tightening forces (restoring forces), and face fasteners 3d', 3f thereof are mutually overlapped and engaged with each other. Furthermore, at this time, the face fastener 3g' of the band-like member 3c' is engaged with the face fastener 2d' of the belt body 2'. By tightening forces of the tightening members 3', 3', the iliac bones H, H are compressed so as to be pushed out in the directions of the arrow (Y) from the abdomen side, whereby the interval between the iliac bones H, H is made narrow to a good health value. Furthermore, as shown in FIG. 4, the end portion of the belt body 2' may be engaged at the abdomen side and the front end portions of the tightening members 3', 3' may be engaged with each other at the back side. At this time, the face fastener 3e' is engaged with the face fastener 2c'.

As described above, according to the use modes shown in FIG. 10 through FIG. 12, the lumbar region are stabilized as by the lumbago correcting belt 1 of the first preferred embodiment, and it is possible to give force vectors starting from the diagonally rearward parts (parts (A) in FIG. 10) or diagonally frrontward parts (parts (B) in FIG. 11) to the lumbar region W by tightening actions of the tightening members 3', 3'. As a result, the iliac bones H, H are pushed out forward or backward, whereby the interval between the iliac bones H, H is adjusted to a good health value. Therefore, it is possible to fundamentally eliminate a cause of lumbago and to remarkably efficiently treat and prevent the same. In particular, these use modes are very effective when feeling a pain when bending back or leaning forward.

Figure 13:
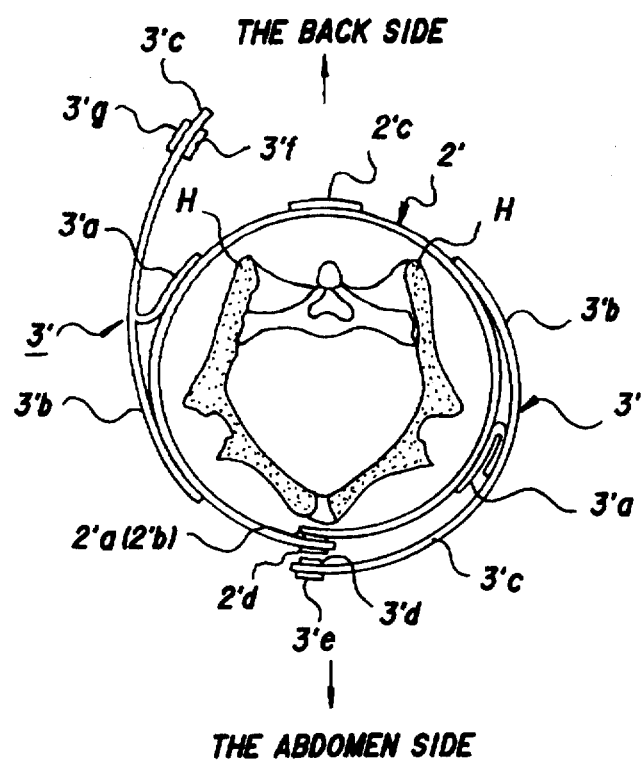
FIG. 13 is a view showing a use mode for a patient who feels a pain when twisting his lumbar region leftward.
Figure 14:
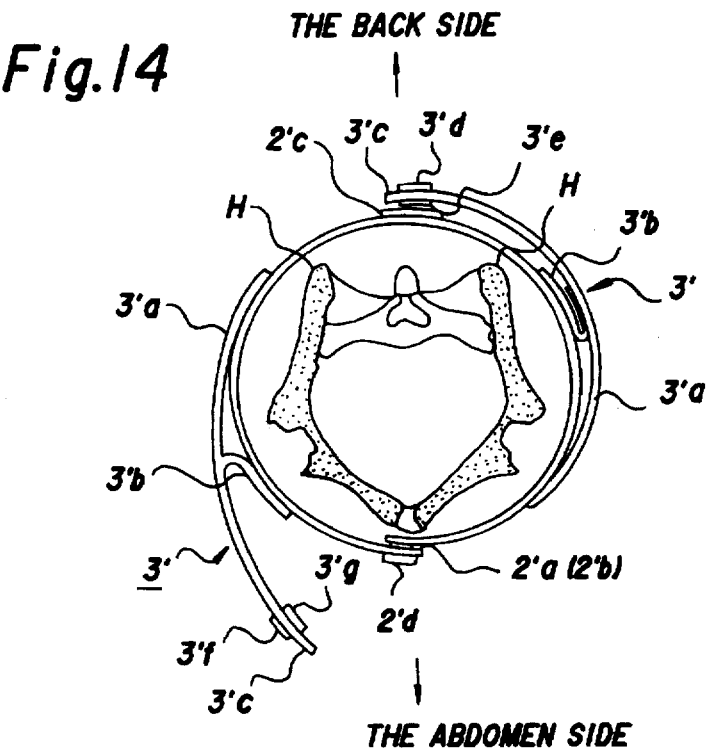
FIG. 14 is a view showing a use mode for a patient who feels a pain when twisting his lumbar region rightward.

On the other hand, when feeling a pain when twisting the lumbar region leftward or rightward, use modes shown in FIG. 13 and FIG. 14 may be selected and used according to the symptoms of a patient. For example, when feeling a pain when twisting leftward, as shown in FIG. 13, after the belt body 2' is wound onto the lumbar region W and is tightened with an adequate tightening force, the face fasteners 2a', 2b' thereof are engaged with each other at the abdomen side. And after the belt body 2' is thus attached to the lumbar region W, the band-like member 3c' of one of the pair of tightening members 3' (the left side tightening member 3' in FIG. 13) is turned to the backside, the face fastener 3f' thereof is engaged with the face fastener 2c' of the belt body 2'. Furthermore, the band-like member 3c' of he other of the pair of tightening members 3' (the right side tightening member 3' in FIG. 13) is turned to the abdomen side, and the face fastener 3d' thereof is engaged with the face fastener 2d' of the belt body 2'.

In other mode, when feeling a pain when twisting the lumbar region rightward, as shown in FIG. 14, firstly, after the belt body 2' is wound onto the lumbar region W and is tightened with an adequate tightening force, the face fasteners 2a', 2b' thereof are engaged with each other at the abdomen side. And the band-like member 3c' of one of the pair of tightening members 3' (the right side tightening member 3' in FIG. 14) is turned to the backside, the face fastener 3e' thereof is engaged with the face fastener 2c' of the belt body 2'. Furthermore, the band-like member 3c' of the other of the pair of tightening members 3' (the left side tightening member 3' in FIG. 14) is turned to the abdomen side, and the face fastener 3g' thereof is engaged with the face fastener 2d' of the belt body 2'.

Thus, since a use mode shown in FIG. 13 or FIG. 14 is used when feeling a pain when the lumbar region is twisted leftward or rightward, it is possible to expand the range of application for treatment and prevention.

Figure 15A:
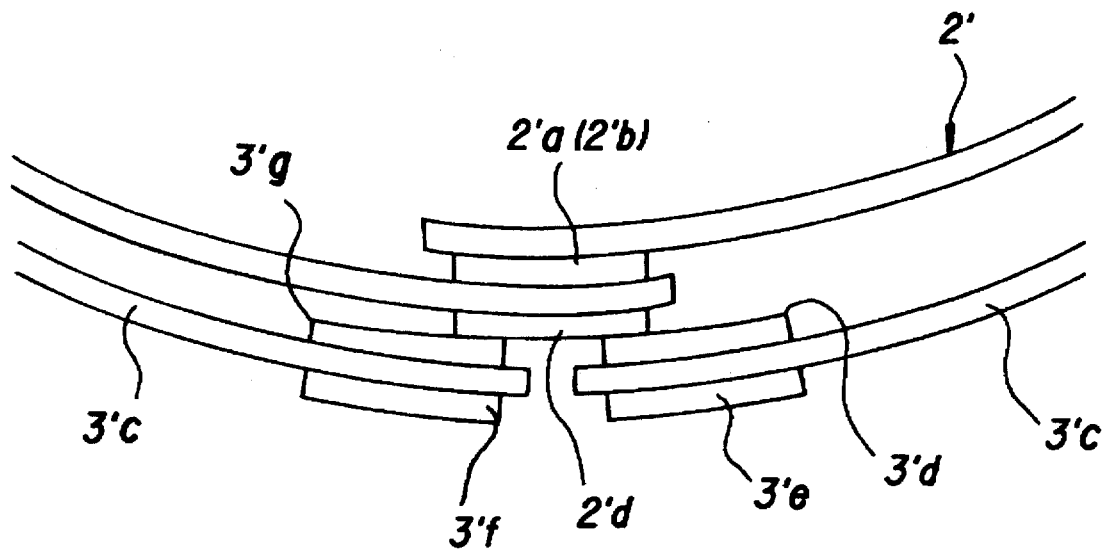
FIGS. 15 are views showing adjusted states of a tightening force of a tightening member, wherein (a) is an enlarged view of major parts showing a state where the tightening force is loose, and (b) is an enlarged view of major parts showing a state where the tightening force is intensive.
Figure 15B:
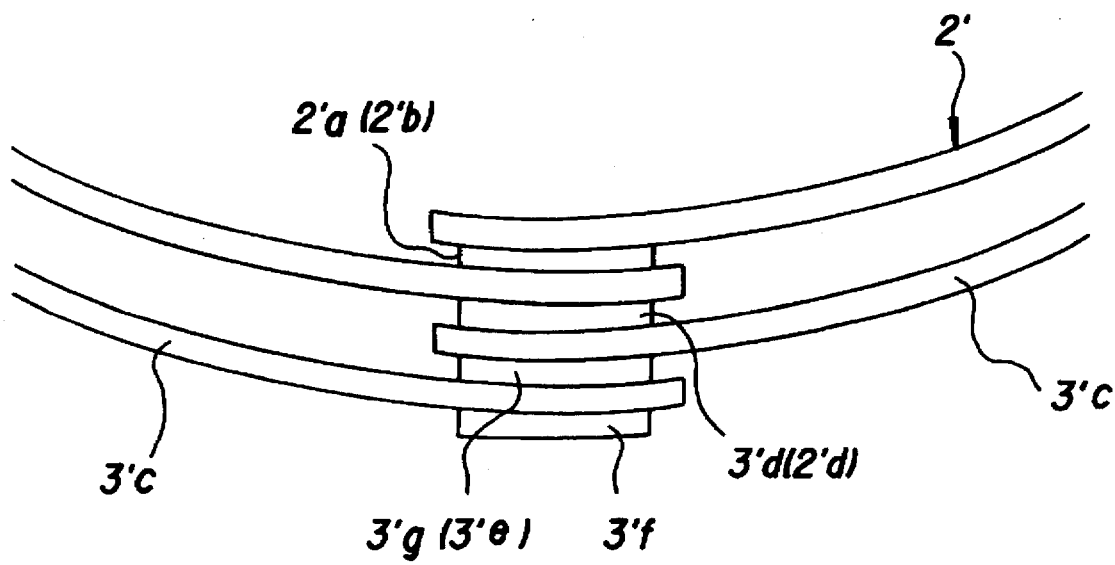

Especially, in the abovementioned use modes, since it is possible to change the tightening forces of the tightening members 3', an adequate treatment is able to be achieved. That is, FIG. 15(a) shows a state where the tightening forces are set to be loose, wherein restricted portions of the face fasteners 3d', 3g' of the band-like member 3c' are overlapped at and engaged with both ends portions of the face fastener 2d' of the belt body 2'. When it is desired that the tightening forces are set to be intensive, as shown in FIG. 15(b), the face fastener 3d' of the band-like member 3c' is engaged with the face fastener 2d' of the belt body 2', and the face fastener 3g' of the band-like member 3c' is engaged with the face fastener 3e' of the band-like member 3c', respectively.

Furthermore, the modified examples shown in FIG. 5 through FIG. 8 in connection with the first preferred embodiment also are applicable to the tightening member in the second preferred embodiment.

Furthermore, face fasteners are preferable as engaging means (2a, 2b, 3d, 3e, 2a', 2b', 2c', 2d', 3d', 3e', 3f', 3g') in the first and second preferred embodiments. However, they are not limited to the same. Any type of elements having such a structure by which they are engageable with each other, such as female and male hooks, buttons, strings or the like, may be employed.

What is claimed is:

1. A lumbago correcting belt, comprising:
 a belt body adapted to be attached to a lumbar region of a human body to enclose and surround iliac bones; and
 a pair of tightening members made of a flexible material, said tightening members being disposed and spaced from each other on an outer circumferential face of said belt body, each of said tightening members having two legs branched therefrom in opposite circumferential directions with reference to said outer circumferential face of said belt body, said two legs compressing iliac bones from appointed directions by a tightening force selectively given to only one of said two legs of each of said tightening members.

2. The lumbago correcting belt as set forth in claim 1, wherein said pair of tightening members are movably disposed on said belt body.

3. The lumbago correcting belt as set forth in claim 1, further comprising a first set of engaging means, one member of which is provided at one end portion of said belt body on said outer circumferential face thereof and another member of which is provided at the other end portion of said belt body on an inner circumferential face thereof, and a second set of engaging means provided on said tightening members at one face of front end portions thereof.

4. The lumbago correcting belt as set forth in claim 3, wherein said pair of tightening members arm movably disposed on said belt body.

5. A method of correcting lumbago in a human, comprising:
 (a) providing a lumbago correcting belt, comprising:
  a belt body adapted to be attached to a lumbar region of a human body to enclose and surround iliac bones,
  a first set of engaging means, one member of which is provided at one end portion of said belt body on an outer circumferential face thereof and another member of which is provided at the other end portion of said belt body on an inner circumferential face thereof,
  a pair of tightening members made of a flexible material, said tightening members being disposed and spaced from each other on an outer circumferential face of said belt body, each of said tightening members having two legs branched therefrom in opposite circumferential directions with reference to said outer circumferential face of said belt body, said two legs compressing the iliac bones from appointed directions by a tightening force selectively given to only on of said two legs of each of said tightening members, and
  a second set of engaging means provided on said tightening members at one face of front end portions thereof;
 (b) contacting the belt body with the lumbar region; and
 (c) engaging said first set of engaging means with each other and engaging said second set of engaging means with each other.

6. The method as set forth in claim 5, wherein said pair of tightening members are movably disposed on said belt body.

7. The method as set forth in claim 5, wherein members of said first set of engaging means are engaged with each other and members of said second set of engaging means are engaged with each other at an abdomen side of the lumbar region to compress the iliac bones from a left and right backside of the lumbar region.

8. The method as set forth in claim 7, wherein said pair of tightening members are movably disposed on said belt body.

9. The method as set forth in claim 5, wherein members of said first set of engaging means are engaged with each other and members of said second set of engaging means are engaged with each other at a back side of the lumbar region to compress the iliac bones from a left and right front side of the lumbar region.

10. The method as set forth in claim 9, wherein said pair of tightening members are movably disposed on said belt body.

11. The lumbago correcting belt as set forth in claim 1, further comprising a first set of engaging means, a first member of which is provided at one end portion of said belt body on said outer circumferential face thereof, a second member of which is provided at the other end portion of said belt body on said outer circumferential face thereof, a third member of which is provided at the other end portion of said belt body on an inner circumferential face thereof and a fourth member of which is provided at a middle portion of said belt body on said outer circumferential face thereof, and a second set of engaging means provided on said tightening members at both faces of front end portions thereof.

12. The lumbago correcting belt as set forth in claim 11, wherein said pair of tightening members are movably disposed on said belt body.

13. A method of correcting lumbago in a human, comprising:

(a) providing a lumbago correcting belt, comprising:
   a belt body adapted to be attached to a lumbar region of a human body to enclose and surround iliac bones,
   a first set of engaging means, a first member of which is provided at one end portion of said belt body on an outer circumferential face thereof, a second member of which is provided at the other end portion of said belt body on said outer circumferential face thereof, a third member of which is provided at the other end portion of said belt body on an inner circumferential face thereof and a fourth member of which is provided at a middle portion of said belt body on said outer circumferential face thereof,
   a pair of tightening members made of a flexible material, said tightening members being disposed and spaced from each other on an outer circumeferential face of said belt body, each of said tightening members having two legs branched therefrom in opposite circumferential directions with reference to said outer circumferential face of said belt body, said two legs compressing the iliac bones from appointed directions by a tightening force selectively given to only one of said two legs of each of said tightening members, and
   a second set of engaging means provided on said tightening members at both faces of front end portions thereof;

(b) contacting the belt body with the lumbar region; and (c) engaging said first set of engaging means with each other and engaging said second set of engaging means with each other.

14. The method as set forth in claim 13, wherein said pair of tightening members are movably disposed on said belt body.

15. The method as set forth in claim 13, wherein members of said first set of engaging means are engaged with each other and members of said second set of engaging means are engaged with each other at an abdomen side of the lumbar region to compress the iliac bones from a left and right backside of the lumbar region.

16. The method as set froth in claim 15, wherein said pair of tightening members are movably disposed on said belt body.

17. The method as set forth in claim 13, wherein members of said first set of engaging means are engaged with each other and members of said second set of engaging means are engaged with each other at a back side of the lumbar region to compress the iliac bones from a left and right front side of the lumbar region.

18. The method as set forth in claim 17, wherein said pair of tightening members are movably disposed on said belt body.

19. The method as set forth in claim 13, wherein one of said second set of engaging means on one of said pair of tightening members is engaged with said fourth member of said first set of engaging means and another of said second set of engaging means on the other of said pair of tightening members is engaged with one of said first set of engaging means selected from the group consisting of said first member and said second member, to compress the iliac bones in a leftward or rightward twisting direction relative to the lumbar region.

20. The method as set forth in claim 19, wherein said pair of tightening members are movably disposed on said belt body.

* * * * *